United States Patent [19]

Hudlicky et al.

[11] Patent Number: 5,442,079
[45] Date of Patent: Aug. 15, 1995

[54] METHOD FOR PREPARING ERYTHRURONOLACTONE

[75] Inventors: Tomas Hudlicky; Martin Mandel, both of Blacksburg, Va.

[73] Assignee: Virginia Polytechnic Institute and State University, Blacksburg, Va.

[21] Appl. No.: 60,454

[22] Filed: May 10, 1993

[51] Int. Cl.$^6$ ............................................. C07D 493/04
[52] U.S. Cl. .................................... 549/306; 549/311
[58] Field of Search ................................ 549/306, 311

[56] References Cited

U.S. PATENT DOCUMENTS 4,111,958  9/1978  Crawford ........................ 260/340.7

Primary Examiner—C. Warren Ivy
Assistant Examiner—Ba K. Trinh
Attorney, Agent, or Firm—Margaret A. Horn

[57] ABSTRACT

There are described improved processes for the synthesis of a desired lactone useful as a synthon, the improved processes comprising oxidizing a protected arene diol with permanganate and periodate or subjecting a substituted epoxydiol to periodate oxidation to yield the desired lactone.

9 Claims, No Drawings

METHOD FOR PREPARING ERYTHRURONOLACTONE

FIELD OF THE INVENTION

This invention relates to improved methods for the synthesis of a useful intermediate lactone 4 and derivatives thereof. More particularly, the improved process of the present invention comprise synthesizing the lactone 4 by controlled oxidation of an epoxide with an effective amount of sodium periodate. Specifically the improved process combines the protection of diol 10, its oxidation to 9, and the subsequent oxidative cleavage to 4 in one operation.

BACKGROUND OF THE INVENTION

The microbial oxidation of aromatic hydrocarbons to corresponding homochiral cyclohexadiene diols with mutant strains of *Pseudomonas putida*, discovered in the late 1960's by Gibson (Gibson, D. T., Hensley M., Yoshika H., Mabry, R. J., Biochemistry 9:1626 (1970)), opened new horizons in syntheses of chiral oxygenated compounds (see for example U.S. patent application Ser. No. 07/974,057, which is incorporated herein by reference). The utility of these chiral oxygenated compounds, which are versatile synthons, is reinforced by their use in enantiocontrolled syntheses as evidenced by several recent reviews. (Brown, M.S., "Organic Synthesis: Theory and Practice" (Hudlicky, T., Ed.), Vol. 2, 113, JAI Press, Greenwich, Conn. (1993); Carless, H. A. J., Tetrahedron: Asymmetry 3:795 (1992); Widdowson, D. A., Ribbons, D. W., Thomas, S. D., Janssen Chimica Acta 8:3 (1990)).

In the carbohydrate field the use of these chiral oxygenated synthons has recently been demonstrated in the preparation of cyclitols (see U.S. patent application Ser. No. 802,783, incorporated herein by reference), as well as four and five membered sugars such as protected L-erythrose 1 and its enantiomer (see U.S. Pat. No. 5,200,516 incorporated herein by reference), protected L-erythrolactone 2 (Hudlicky, T., Luna, H., Price, J. D., Rulin F., Tetrahedron Lett. 30:4053 (1989) and protected L-ribonic γ-lactone 3 (Hudlicky, T., Price J. D., Synlett 159 (1990)). 2,3-O-Isopropylidene-L-erythruronolactone 4 is a versatile chiral synthon that has been used in many enantioselective syntheses including the preparation of compounds 1, 2, and 3 shown below and (−)-trihydroxyheliotridane 5 (Hudlicky, T., Luna, H., Price, J. D., Rulin, F., J. Org. Chem. 55:4683 (1990); and enone 6 (Hudlicky, T., Natchus, M. G., Nugent, T. C., Synth. Commun. 22: 151 (1992) used in the synthesis of PGE$_{2\alpha}$ (Hudlicky, T., Luna, H., Barbieri, G., Kwart, L. D., J. Am. Chem. Soc. 110:4735 (1988); Johnson, C. R., Penning, T. D., J. Am. Chem. Soc. 108:5655 (1986)) and specionin (Hudlicky, T., Natchus, G. M., J. Org. Chem. 57:4740 (1992)). Recently, compound 4 appeared to be of particular interest as the key intermediate in the synthesis of dipeptide renin inhibitor, dihydroxyethylene isostere (Baker, W. R., Condon, S. L., Tetrahedron Lett. 33:1581 (1992) 7.

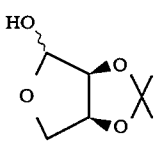

1

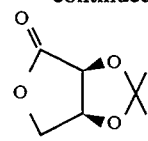

2

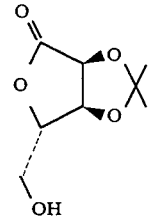

3

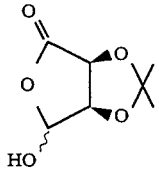

4

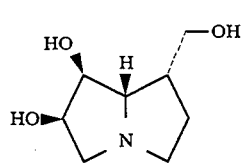

5

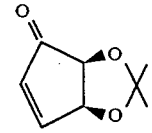

6

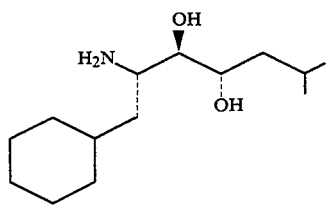

7

Known methods for the preparation of 4 include syntheses starting from ribonolactone (Beer, D., Meuwly, R., Vasella, A., Helv. Chim. Acta 65:2570 (1982)), chlorobenzene (Hudlicky, T., Luna, H., Price, J. D., Rulin, F., Tetrahedron Lett. 30:4053 (1989); Hudlicky, T., Luna, H., Price, J. D., Rulin, F., J. Org. Chem. 55:4683 (1990)) and D-gulonolactone (Borchardt, R. T., Wolfe, M. S., Anderson, B. L., Borcherding, D. R., J. Org. Chem. 55:4712 (1990); Borchardt, R. T., Borcherding, D. R., Scholtz, S. A., J. Org. Chem. 52:5457 (1987)) (cyclohexylidene protection group)); however, many of these routes are problematic in that they comprise multiple steps, are not scaleable to commercial levels or use environmentally undesirable reagents or conditions. The procedure of the present invention appears to be effective in both cost and the use of environmentally acceptable protocol and, therefore, is a desirable improvement over that known in the art.

SUMMARY OF THE INVENTION

One embodiment of the present invention comprises a process for the synthesis of a desired lactone, the process comprising reacting an epoxide of the formula:

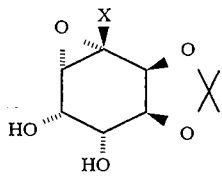

wherein X is H, halogen, OR, NR$_2$ or CN, where R and R$_2$ are each independently lower alkyl (C1–C5) or aryl, with an effective amount of periodate in a substantially aqueous environment and recovering the desired lactone product or an enantiomer thereof. Preferably X is Cl or Br.

In a preferred embodiment of the present invention, the permanganate is KMnO$_4$ and the periodate is selected from the group consisting of NaIO$_4$, KIO$_4$ or LiIO$_4$. Most preferably, the reaction resulting in the production of the desired lactone is a one pot reaction.

DETAILED DESCRIPTION OF THE INVENTION

As described previously, the desired lactone 4 of the present invention is a known compound, however, the synthetic processes currently available have certain limitations. Scheme 1 below shows an earlier reported method for making the lactone 4 from the chlorobenzene diol acetonide 8 using ozonolysis (U.S. Pat. No. 5,200,516). Although yields of 4 were good (73%), ozonolysis may not be desirable for commercial production.

Recently we have reported that the oxidation of chlorobenzene diol acetonide 8 with permanganate (U.S. patent application Ser. No. 974,057) yielded an unusual chloroepoxide 9 (Scheme 1). Among other interesting transformations (Hudlicky, T., Mandel, M., Lee, R. S., Bachman, B., Dudding, T., Merola, J., Manuscript in preparation), this compound 9 has now been found to be a useful intermediate in the synthesis of erythruronolactone 4 via a unique oxidation of the diol-chloroepoxide moiety with periodate (Scheme 1).

While Scheme 1 demonstrates the process with a chloroepoxide and starting from chlorobenzene, it is understood that other substituted diols and the resulting substituted epoxides, as described above in the Summary of the Invention, may be used in the present invention. In other words, the substituent at the 1 position of the diol compound 10 is X where X is halogen, OR, NR$_2$ or CN (where R and R$_2$ each are lower alkyl or aryl). Therefore, the acetonide (8a) shown in Scheme 1 could also be substituted at the 1 position with X, wherein X is as defined above. This X substituted acetonide is referred to as compound 8 hereinafter.

Likewise, although Scheme 1 shows the reaction of compound 8a with potassium permanganate and the reaction of compound 9a (X=Cl) with sodium periodate, those skilled in the art would readily recognize other reagents which would result in similar oxidation. For example, periodates useful in the present invention include but are not limited to NaIO$_4$, KIO$_4$, LiIO$_4$ or any other metal periodate.

Initial work showed that at least about 2 equivalents of periodate are necessary for complete oxidation of chloroepoxide 9a, while lesser amounts of periodate led to the recovery of the starting material. No intermediate was observed (TLC) during monitoring of these reactions. Larger amounts of periodate did not increase the yield, nor change the amount of byproducts, which were separated by extraction of basified reaction mixtures of EtOAc. Thus, as used herein, an "effective amount of periodate" means at least about 2 equivalents of periodate. Without intending to be limited to any particular mechanism of action of the process shown in Scheme 1, the proposed oxidative degradation of compound 9a to compound 4 is depicted in Scheme 2. Although speculative, it explains the formation of lactone 4 through intermediates analogous to those invoked in the breakdown of ozonides derived from ozonolysis of 8 (Hudlicky, T., Luna, H., Price, J. D., Rulin, F., J. Org. Chem. 55:4683 (1990)) and related compounds (Hudlicky, T., Luna, H., Barbieri, G., Kwart, L. D., J. Am. Chem. Soc. 110:4735 (1988)).

Scheme 1.
Synthesis of 2,3-Isopropylidene-L-erythruronolactone (4).

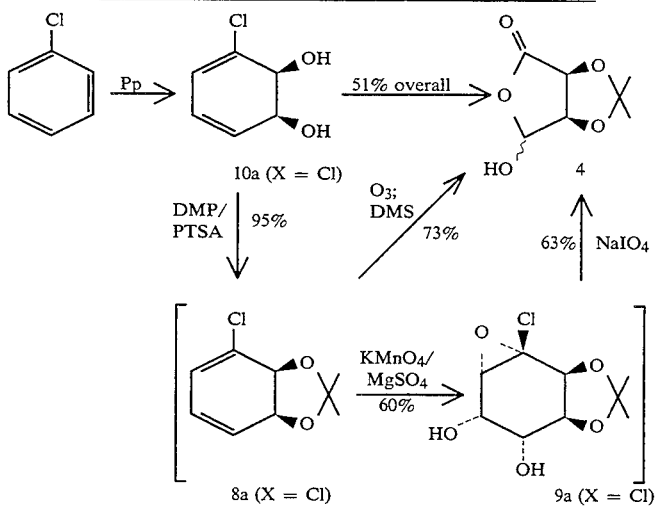

Scheme 2.
Proposed Mechanism for the Oxidative Degradation of 9a to 4.

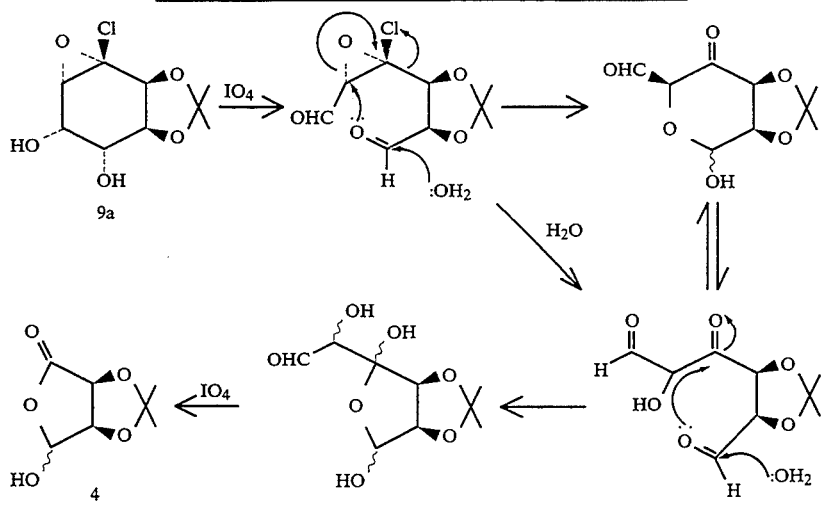

The reactions described in the present invention may be carried out using suitable or appropriate solvents which include but are not limited to water, water miscible solvents such as dialkylketones with 2-4 carbon atoms, lower alcohols with 1-3 carbon atoms, cyclic ethers and ethers with 2-6 carbon atoms, or mixtures thereof. Preferably, the reactions are carried out in a substantially aqueous environment, which as used herein means an environment having a sufficient amount of water to provide adequate solubility of the periodate, understanding that if one increases or decreases the equivalents of periodate used, a corresponding change in the amount of water used in the reaction may be made.

The reaction of the acetonide 8 with permanganate to yield the epoxide 9 is fully described in U.S. patent application Ser. No. 07/974,057, the disclosure of which is incorporated herein by reference. Generally, the acetonide is exposed (contacted) to permanganate in an appropriate solvent (as defined above) at an appropriate temperature (from about $-78°$ C. to $+40°$ C.).

Any permanganate may be useful in the present invention provided it results in the desired oxidation, for example, any permanganate having the formula $M(MnO_4)_n$ (where M is $R_4N^+$, K, Na, Li, Me, Ca, Zn, etc., and n is 1 or 2) would be useful in the present invention. Potassium permanganate is a preferred reagent. An effective amount of permanganate will vary depending on what permanganate is used, however, when $KMnO_4$ is used, an effective amount means at least about 1.5 equivalents.

As will be understood by those skilled in the art, the pH of the reaction mixture may affect the stability of a desired compound. Any known method for controlling pH can be used, for example a buffering agent or system can be used to maintain a suitable pH range, or one could saturate the reaction mixture with $CO_2$ or buffer the reaction mixture using an organic or inorganic weak acid.

As provided in Scheme 1 above, on a 10 g scale the oxidation furnished erythruronolactone 4 with crude yield higher than 60% and purity comparable, if not superior, to the product obtained previously by ozonolysis of the diene 8 (U.S. Ser. No. 480,891). A preferred method for producing this high quality product comprises a more direct preparation without the isolation of intermediates 8 and 9. Thus, the entire reaction sequence of protection and beth permanganate and periodate oxidation of the chlorobenzene diol 10 (10 g scale preparation) was realized as a one-pot sequence with the overall yield higher than 50%.

(The crude yield of optimized discontinuous ozonolysis (Mandel, M., Hudlicky, T., unpublished observations) ranges 70–75% on 20 g scale). As a result, technologically arduous and environmentally hazardous oxidation of diene with ozone was replaced by an easily manageable procedure using significantly less toxic reagents with good potential for further optimization.

EXPERIMENTAL

The optical rotation data were measured using a Perkin Elmer 241 Polarimeter, melting point was determined on the Thomas Hoover Capillary Melting Point Apparatus. TLC system used throughout was MeOH:$CHCl_3$, 1:9.

2,3-O-Isopropylidene-L-erythruronolactone (4). Method A. The mixture of chloroepoxide 9a (Mandel. M., Hudlicky, T., Kwart, L. D., Whited, G. M., J. Org. Chem 58 (1993), in press) (10.0 g, 42.3 mmol), water (200 ml) and $NaIO_4$ (19.0 g, 88.8 mmol) was stirred at ambient temperature for 4 h, while a slight stream of argon was bubbled through. After the reaction was complete, pH was adjusted to 7.5 (5N NaOH) and the mixture was extracted with EtOAc (3x). The water layer was acidified to pH 2 (HCl 1:1), the solution was quickly saturated with NaCl and extracted with EtOAc (6x). Combined extracts were dried over $MgSO_4$ and evaporated under reduced pressure to give crystalline product (4.63 g, 63.2%), m.p. 82°–90° C. Recrystallization (toluene/hexane; (5.5 ml/g)/(4 ml/g), 85% recovery) gave product with m.p. 101°–103° C. and $[\alpha]_D^{25}$ +31 ° (C=1, $CHCl_3$).

Method B. The mixture of chlorobenzene diol 10 (Hudlicky, T., Boros, C. H., Boros, E. E., Synthesis 174 (1992)) (10.0 g, 68.2 mmol), acetone (100 ml), 2,2-dimethoxypropane (22.6 ml, 184.2 mmol) and p-toluenesulfonic acid (0.8 g, 0.4 mmol) was stirred for 20 min at ambient temperature. The resulting solution was cooled to 0° C. and added dropwise over the period of 15 min to a mixture of $KMnO_4$ (24.8 g, 156.9 mmol), $MgSO_4$ (14.0 g, 116.0 mmol), acetone (150 ml) and water (400 ml), precooled to −12° C. The temperature of the reaction mixture was maintained below 0° C. by controlling the rate of addition. The excess of permanganate was titrated with saturated solution of NaHSO$_3$ and the mixture was stirred at 0° C. for 10 min and then filtered. To the resulting, slightly yellowish solution was added NaIO$_4$ (38.2 g, 178.6 mmol) and the mixture was stirred at ambient temperature for 2 h (at the end of the reaction, pH of the mixture was 3–4). The pH was adjusted to 7.5 (5N NaOH), the mixture was extracted with EtOAc (4x), saturated with NaCl and acidified to pH 2 (HCl 1:1). Extraction with EtOAc (10x), drying over MgSO$_4$ and evaporation furnished 6.0 g (50.8%) of the oily product, which turned to crystals identical with the product obtained above.

The use of compound 4 as an intermediate is shown in commonly owned U.S. Pat. No. 5,200,516, FIG. 3 and in the Experimental Section, the entire disclosure of which is incorporated herein by reference.

What is claimed is:

1. A process for the synthesis of a desired lactone (4), the process comprising reacting an epoxide of the formula:

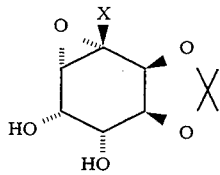

wherein X is halogen;

with an effective amount of periodate in a substantially aqueous environment and recovering the desired lactone (4) or an enantiomer thereof.

2. A process of claim 1 wherein X is Cl or Br.

3. A process of claim 1 wherein the periodate is NaIO$_4$, KIO$_4$ or LiIO$_4$.

4. A process of claim 3 wherein the periodate is NaIO$_4$ present in an amount of at least about 2 equivalents.

5. An improved process for the synthesis of a desired lactone (4) starting from a substituted cyclohexadiene diol substituted at the 1 position of such diol with a halogen substituent, the process comprising: a) protecting the diol as its acetonide compound; b) contacting the acetonide with an effective amount of permanganate in an appropriate solvent to yield an epoxydiol; c) contacting the epoxydiol with an effective amount of periodate; and d) recovering the desired lactone or a racemate thereof.

6. The process of claim 5 wherein the reaction is performed as a one pot reaction.

7. A process of claim 5 wherein the permanganate is KMnO$_4$.

8. A process of claim 5 wherein the periodate is NaIO$_4$, KIO$_4$ or LiIO$_4$.

9. A process for preparing a desired lactone useful as a synthon, the process comprising:
   a) contacting chlorobenzene diol with dimethoxypropane, acetone and p-toluenesulfonic acid with stirring;
   b) adding to the mixture of step a) KMnO$_4$ in the presence of a buffer and a water-miscible solvent; and
   c) adding to the mixture of step b) NaIO$_4$ to yield the desired lactone.

* * * * *